(12) United States Patent
Buzug et al.

(10) Patent No.: US 10,338,161 B2
(45) Date of Patent: Jul. 2, 2019

(54) METHOD FOR MAGNETIC PARTICLE IMAGING HAVING UNLIMITED AXIAL FIELD OF VIEW

(71) Applicant: UNIVERSITAET ZU LUEBECK, Luebeck (DE)

(72) Inventors: Thorsten Buzug, Gross Sarau (DE); Christian Kaethner, Luebeck (DE); Mandy Gruettner, Luebeck (DE); Gael Bringout, Luebeck (DE); Matthias Weber, Luebeck (DE)

(73) Assignee: UNIVERSITAET ZU LUEBECK (DE)

( * ) Notice: Subject to any disclaimer, the term of this patent is extended or adjusted under 35 U.S.C. 154(b) by 420 days.

(21) Appl. No.: 15/039,169

(22) PCT Filed: Nov. 29, 2013

(86) PCT No.: PCT/EP2013/075148
§ 371 (c)(1),
(2) Date: May 25, 2016

(87) PCT Pub. No.: WO2015/078527
PCT Pub. Date: Jun. 4, 2015

(65) Prior Publication Data
US 2017/0023651 A1 Jan. 26, 2017

(51) Int. Cl.
*G01R 33/38* (2006.01)
*G01R 33/12* (2006.01)
(Continued)

(52) U.S. Cl.
CPC ........ *G01R 33/1276* (2013.01); *A61B 5/0515* (2013.01); *G01R 33/307* (2013.01); *G01R 33/38* (2013.01)

(58) Field of Classification Search
CPC ............ G01R 33/3415; G01R 33/3692; G01R 33/36; G01R 33/546; G01R 33/1276;
(Continued)

(56) References Cited

U.S. PATENT DOCUMENTS 3,166,707 A * 1/1965 Bonnet .................. G01R 33/24
324/301
3,257,608 A * 6/1966 Bell ....................... G01R 33/26
324/244
(Continued)

FOREIGN PATENT DOCUMENTS

WO WO 2011/030249 A1 3/2011

OTHER PUBLICATIONS

International Search Report prepared by the European Patent Office dated May 12, 2014, for International Application No. PCT/EP2013/075148.

*Primary Examiner* — Patrick Assouad
*Assistant Examiner* — Taqi R Nasir
(74) *Attorney, Agent, or Firm* — Sheridan Ross P.C.

(57) ABSTRACT

The invention relates to a method and an MPIS scanner for tomographic imaging of an object with magnetic particles distributed in the interior of the object, comprising the steps of generating a selection magnetic field with a predetermined magnetic field gradient in at least one field-free point (FFP) in a predetermined scanning plane, generating a time-dependent, periodic excitation magnetic field with a predetermined maximum frequency, repeatedly displacing the at least one FFP along a predetermined closed trajectory with a predetermined repetition time in the scanning plane, moving the object through the scanning plane along a predetermined advance direction with a predetermined advance speed, detecting the change in the magnetization state of the magnetic particles at the points in the object interior through which the at least one FFP passes, recon-
(Continued)

structing the local particle concentrations at the points through which the at least one FFP passes in respect of an object coordinate system, interpolating the reconstructed particle concentration to the points in the object interior not passed through by at least one FFP, generating a display of the particle concentration distribution in the object interior, characterized by interpolating the particle concentrations reconstructed at path section end points of path sections along the advance direction to path section intermediate points taking into account the advance speed.

15 Claims, 3 Drawing Sheets

(51) Int. Cl.
*A61B 5/05* (2006.01)
*G01R 33/30* (2006.01)
(58) Field of Classification Search
CPC ........ G01R 33/307; G01R 33/38; A61B 6/12; A61B 5/0515
USPC .................................. 324/301, 302, 304, 300
See application file for complete search history.

(56) References Cited

U.S. PATENT DOCUMENTS

| 5,557,199 | A | * | 9/1996 | Bowman | G01R 33/443 |
| | | | | | 324/301 |
| 8,812,078 | B2 | * | 8/2014 | Vernickel | A61B 5/05 |
| | | | | | 324/300 |
| 2011/0089942 | A1 | * | 4/2011 | Goodwill | A61B 5/05 |
| | | | | | 324/301 |
| 2011/0221438 | A1 | * | 9/2011 | Goodwill | G01R 33/10 |
| | | | | | 324/301 |
| 2012/0153948 | A1 | * | 6/2012 | Rahmer | A61B 5/05 |
| | | | | | 324/301 |
| 2012/0153949 | A1 | * | 6/2012 | Biederer | A61B 5/05 |
| | | | | | 324/301 |
| 2016/0081579 | A1 | * | 3/2016 | Schmale | G01R 33/10 |
| | | | | | 324/301 |

* cited by examiner

METHOD FOR MAGNETIC PARTICLE IMAGING HAVING UNLIMITED AXIAL FIELD OF VIEW

CROSS REFERENCE TO RELATED APPLICATIONS

This application is a national stage application under 35 U.S.C. 371 and claims the benefit of PCT Application No. PCT/EP2013/075148 having an international filing date of Nov. 29, 2013, which designated the United States, the disclosure of which is incorporated herein by reference.

BACKGROUND OF THE INVENTION

The invention relates to a method for tomographic imaging of an object having magnetic particles distributed in the interior of the object.

BRIEF SUMMARY OF THE INVENTION

The method of Magnetic Particle Imaging (MPI) determines local concentrations of magnetizable nanoparticles in an a priori unknown spatial distribution in the interior of an object. For example super-paramagnetic iron oxide particles in an investigation region can be magnetized periodically by a magnetic field that can be changed periodically with a predetermined frequency, also called drive field below, the magnetization of the particles being a non-linear function of the total magnetic field strength. If the temporal behavior of the particle magnetization is detected and analyzed e.g. using detection coils, the measurement signal exhibits higher harmonics of the frequency of the drive field and the particle concentration can be inferred from a Fourier analysis of the signal. As an alternative, the image reconstruction can also take place using the x-Space method.

For limiting relatively small volumes of the investigation region, the drive field is superposed by a—usually temporally constant—selection field. At least one predetermined point of the investigation region, the selection field exhibits a Zero. Starting from this so-called field-free point, FFP for short, the selection field rises quickly in all directions so that the magnetizable nanoparticles reach magnetic saturation even at a low distance from the FFP. Nanoparticles at a great distance from the FFP then hardly react any longer to the drive field and do not make any significant contribution to the detected signal. The MPI signal rather originates from the local vicinity of the FFP and provides information on the local particle concentration that is present there.

Using the drive field, the FFP is shifted inside the investigation region; the FFP here traverses a trajectory, that can be open, however as a rule is closed, so that the FFP returns to its starting point after predetermined repetition time. The drive field is time-dependent and is usually generated using electromagnets.

BRIEF DESCRIPTION OF THE SEVERAL VIEWS OF THE DRAWINGS

The following figures are used for further illustration. In the figures:

FIG. 1 $a$) shows the magnetization curve M(x) of a super-paramagnetic iron oxide particle in the vicinity of an FFP in the case of x=0, that exhibits a predetermined magnetic-field gradient G, and FIG. 1 $b$) shows the derivation dM/dx;

FIG. 2 $a$) shows a two-dimensional Lissajous trajectory having crossing points in the scan plane, and FIG. 2 $b$) shows the expanded FFP trajectory associated with FIG. 2 $a$), along which the measurement data are detected in the object coordinate system.

DETAILED DESCRIPTION OF THE INVENTION

Figure 1:
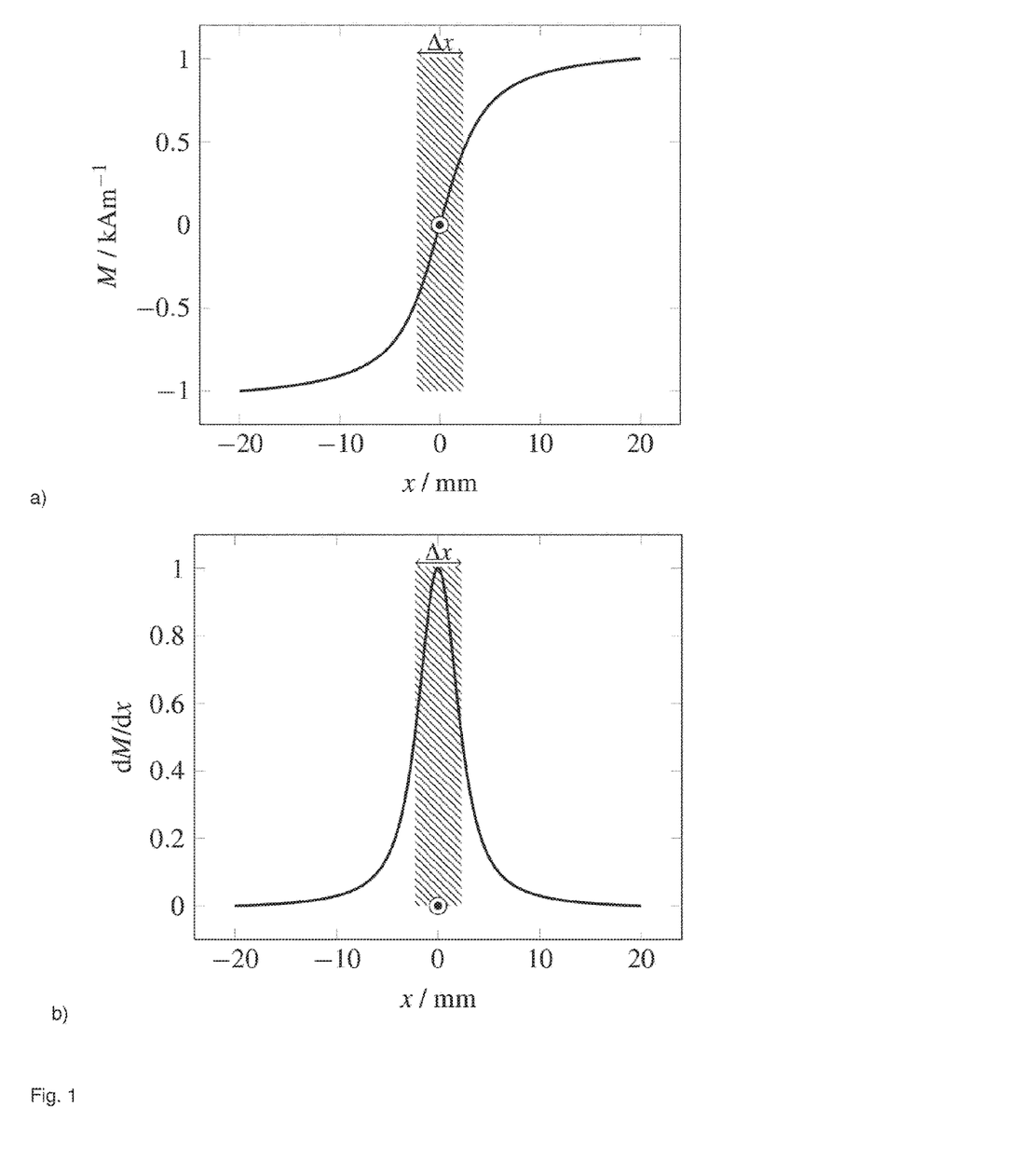

FIG. 1 $a$) illustrates a typical magnetization curve of super-paramagnetic iron oxide particles. Under the action of a selection field that establishes an FFP having a magnetic-field gradient G at x=0, the magnetization of a particle approximates the curve of a Langevin function. It is unsaturated magnetically only in the vicinity of the width Δx about the FFP and shows a response to the drive field of the MPI. The width Δx is usually equated with the peak width of the derivative dM/dx that in turn is defined as the distance of the two values dM/dx=½ (called full width half maximum FWHM), as illustrated in FIG. 1 $b$). The derivative of the magnetization curve is also called the point spread function. A punctiform particle can in principle only be localized down to the precision of one interval using an MPI measurement.

As can be gathered from FIG. 1 $a$) and FIG. 1 $b$), a higher magnetic-field gradient G in the FFP also entails a steeper curve of the Langevin function as a result of x=0 and thus a smaller peak. Since the Langevin function about x=0 is linear in the leading order, Δx and G exhibit there a mutually anti-proportional behavior. The proportionality constant is an attribute of the particles used, the so-called magnetic effectiveness Xs.

$$\Delta x = X_S / G \qquad (1)$$

The magnetic effectiveness of a type of particle is usually already known. Else it can also be determined simply by prior experiments. A usual value for the contrast medium Resovist is e.g. $X_S = 3 \times 10^{-3}$ T, i.e. at a magnetic-field gradient of G=1 T/m the width of the point spread function amounts to approximately 3 millimeters.

The Field of View (FOV) of an MPI-measurement device, also called MPI scanner below, is the spatial area across which an FFP can sweep during the course of the measurement. The FOV can be smaller or greater than the volume of an object to be measured. During the measurement process, the change of the magnetization state of the magnetic particles distributed in the object is detected and continually registered using the current position of the FFP. In the process, not each spatial point of the FOV is necessarily swept by an FFP, but in the ideal case an FFP at some point in time gets close enough to each of the spatial points that also particle concentrations from the spatial points not swept provide signal contributions.

In practice, the FOV is usually subdivided into cube-shaped voxels having the edge length Δx (as defined above) or smaller and it is attempted to sense at least one MPI measurement value for each voxel in the interior of the object. An FOV that has been scanned in this way can then be interpolated—typically linearly—without any problems, i.e. between in each case two spatial points for which concentration values determined by means of MPI are available, concentration values having a distance-dependent weighting can be estimated reliably on spatial points lying in between. The prescribed procedure for MPI measurement value detection in almost each voxel is to be described below also as a "sufficiently dense" sampling of the FOV.

For example from U.S. 2012/153949 A1 it is known that Lissajous trajectories can be generated along orthogonal axes (e.g. x and y axes) by means of two harmonically time-dependent homogenous magnetic fields, wherein the preferred trajectories for MPI exhibit numerous crossing points and for example satisfy the condition $$fy/fx = Nd/(Nd+1) \quad (2)$$

Here fx and fy refer to the frequencies along the x and y axes. Nd is a natural number, and the number of crossing points of the trajectory then amounts to approximately Nd*Nd. Starting from a frequency ratio fy/fx>0.98 the term "high density" trajectory is used.

The FOV of an MPI scanner having such a trajectory is essentially two-dimensional—to be precise a layer having the thickness $\Delta x$ is scanned—and is usually of an approximately square shape. The FFP moves in a plane that is also called scan plane below. The diameter of the FOV, i.e. the maximum distance of two spatial points traversed by the FFP on the trajectory, is smaller than the distance of the coils that generate the drive fields, and can in particular also be made to be much smaller.

In order to scan the two-dimensional FOV of an MPI scanner with sufficiently density, that is generated by a Lissajous trajectory having crossing points and a predetermined diameter, the magnetic effectiveness of the magnetizable particles have to be known and the magnetic-field gradient in the FFP has to be selected such that the width $\Delta x$ of the point spread function approximately coincides with the distance of neighboring lines of the trajectory or with the distance of neighboring crossing points.

An MPI scanner can also be provided with a three-dimensional FOV in that a further coil pair is provided and a transition is made to a three-dimensional trajectory.

The work by Borgert J., Gleich B., Rahmer J., Dahnke H., Weizenecker J., "Three-Dimensional Real-Time In Vivo Magnetic Particle Imaging", MedicaMundi, 53/2, 2009, p. 48-57 reveals an MPI scanner that exhibits coils for generating and superposing three homogenous magnetic fields that are directed at right angles to each other, using which the FFP can be positioned arbitrarily inside a three-dimensional FOV. In this way an MPI volume scan can be carried out at a predetermined measuring-point density. It is proposed in particular to move the FFP along a three-dimensional Lissajous figure as trajectory in that a harmonic oscillation is modulated on each homogenous magnetic-field component and the three frequencies are set to be commensurable. However, the dimensions, achievable so far, of the FOV are relatively small; they amount to only a few centimeters.

As an alternative, a three-dimensional FOV can be realized in that there is provided at an MPI scanner a device for shifting the object through a scan plane that is two-dimensional as described above. There is for example used a bench that can be shifted by means of electric drives, on which the object placed thereon is moved through a coil arrangement that generates a magnetic field. In this case, the usually two-dimensional FOV of the MPI scanner is expanded along the feed direction, it being convenient to carry out the registration of the MPI measurement data in a coordinate system that is firmly associated with the object, also called object coordinates below.

The work by Goodwill, P. W., Konkle, J. J., Zheng, B., Saritas, E. U., Conolly, S. M., "Projection X-Space Magnetic Particle Imaging", IEEE Trans. Med. Imag., 31(5), 2012 an MPI scanner is known that is designed to generate field-free lines, FFL for short, by means of quadrupole selection fields. An FFL can be regarded as a sequence of a multiplicity of FFPs along a line. In analogy to FFPs, it can be shifted by means of homogenous magnetic drive fields, but also rotated by varying the quadrupole magnetic field e.g. about a pivot point in the center of the line. On top of this—as it is also mentioned in WO 2010/008478 A2—also mechanically shifting the FFL by means of the object to be measured can be envisaged. In the work by Goodwill et al. (2012), the patient table (in this case: patient=mouse killed prior to measurement) is moved at a constant velocity of 2.5 cm/s along an axis through the field-generating coil arrangement, while the FFL is reciprocated periodically by magnetic-field modulation in a scan plane at right angles to the bench feed direction. This measurement arrangement, too, exhibits at right angles to the feed direction an FOV having dimensions of only a few centimeters, while the FOV can be expanded in principle to an arbitrary width along the bench feed direction.

For tomographic imaging an object that can be moved through a scan plane, the FOV that is three-dimensional in terms of object coordinates, can likewise be subdivided in typically cubical voxels having an edge length $\Delta x$ or smaller and it can be attempt to assign to each voxel at least one MPI measurement value. Self-evidently, the object will be shifted continuously and the measurement values will be sensed layer by layer until the object area of interest has passed the scan plane.

In the case of the MPI arrangements described above having a three-dimensional FOV, the frequencies, used for scanning, of the drive fields are in each case above 20 kHz. The repetition times of the trajectories are in the order of magnitude of milliseconds, and sufficiently dense sampling of the FOV can be achieved during the course of a few minutes.

This is true especially when using an FFL instead of a single FFP. Even though at first sight an FFL for sampling a large FOV seems particularly suitable because it dispenses with the scan requirement along one of the three space dimensions, it has to be regarded as a disadvantage that only signals are obtained as original MPI measurement data that result as sums of all particle responses along the FFL. The computer-based reconstruction of local particle concentrations and their assignment to voxels inside the FFL can only be achieved by an evaluation that is similar to the image reconstruction of CT images (computer tomography). Obviously it can be expected that measurement data relative to a plurality of differently oriented FFLs have to be detected in each layer of the object, so that particle concentrations can be determined for individual voxels of the layer.

In a future medical application of the MPI method, markedly greater coil distances will have to be realized for tomographic imaging of any body parts or also of the entire body of a patient. For example it can be assumed that the electromagnetic coils will have to exhibit a distance of approximately 0.5 m. Relatively large selection and drive field amplitudes will then have to be generated so that magnetic-field gradients of the order of magnitude up to 1 T/m can be established across the entire FOV. The patient will then have to endure continuous changes in the magnetic field about the orders of magnitude of 0.1 to 1 T in his/her body during the scan process. This can have unwanted side effects.

It is for example known from Reilly, J. P., "Magnetic field excitation of peripheral nerves and the heart: a comparison of thresholds", Med. Bio. Engin. Comp., 29 (6), 571-579, 1991, that time-variable magnetic fields can lead to perceivable—occasionally also painful—peripheral nerve stimulations (PNS). Responsible for this is the induction of electric field gradients in the area of the nerve fibers by magnetic flux density changes dB/dt of the order of magnitude of 100 T/s or higher. Reilly specifies in particular threshold values for triggering the PNS for the flux density amplitudes of sinusoidally oscillating magnetic fields that in turn depend on the oscillation frequency. According to this, in a human MPI scanner the amplitude range 0.1 to 1 T limits the safe—i.e. reliably PNS free—region to field frequencies about 100 Hz, but in any case to the sub-kilohertz range.

While the MPI scanners described above in each case exhibit an FOV having a volume that is markedly smaller than 1 dm$^3$, future medical MPI scanners have to be equipped with a FOV volume in the range 10 to 100 dm$^3$ or more. In addition, in a human full body scanner they will foreseeably be able to use only periodic drive fields that exhibit frequency components of at most 1000 Hz, probably even only a few 100 Hz. Taken together, those will lead to a marked increase of the repetition times of FFP or FFL trajectories and thus enforce that a sufficiently dense sampling of the FOV for an object—possibly of the size of a human person—requires a time span that is 1 to 2 orders of magnitude above those of present lab systems.

In particular for a living patient a very long residence time in an MPI scanner is hardly reasonable. On top of this, long measurement times are a disadvantage even under the aspects of utilization economy of the MPI scanner.

To remedy this, sub-sampling of the FOV can be envisaged so as to accelerate the scan process. This can in turn give rise to artifacts during MPI imaging since with an increase in the degree of sub-sampling it will also be dependent more strongly on data interpolation. The degree of sub-sampling is defined here as the number of voxels of the FOV, to which no MPI measurement value from the MPI scan process can be assigned directly, divided by the number of all voxels of the FOV.

The object of the invention is to propose an MPI method for tomographic imaging with the possibility of sub-sampling the FOV, that comprises an artifact-avoiding interpolation of measured particle concentrations. This is to dispense completely with field-generating coils in the axial direction and to make possible an axially unlimited field of view by a continuous patient-bench feed.

The object is achieved by a method for tomographic imaging an object having magnetic particles distributed in the interior of the object and having a pre-known magnetic effectiveness, comprising the following steps generating a selection field having a predetermined magnetic-field gradient in at least one field-free point (FFP) in a predetermined scan plane, generating a time-dependent, periodic magnetic drive field having a predetermined maximum frequency, repeatedly shifting the at least one FFP along a predetermined closed trajectory having a pre-known repetition time in the scan plane, moving the object through the scan plane along a predetermined feed direction at a predetermined feed velocity, detecting the change in the magnetization state of the magnetic particles at the locations, traversed by the at least one FFP, in the interior of the object, reconstructing the local particle concentrations at the locations, traversed by the at least one FFP, relative to an object coordinate system, interpolating the reconstructed particle concentrations onto the locations, not traversed by at least one FFP, in the interior of the object, generating a representation of the particle concentration distribution in the interior of the object, characterized by interpolating the particle concentrations, reconstructed at path section end points of path sections along the feed direction, onto path section intermediate points taking into account the feed velocity.

Figure 3:
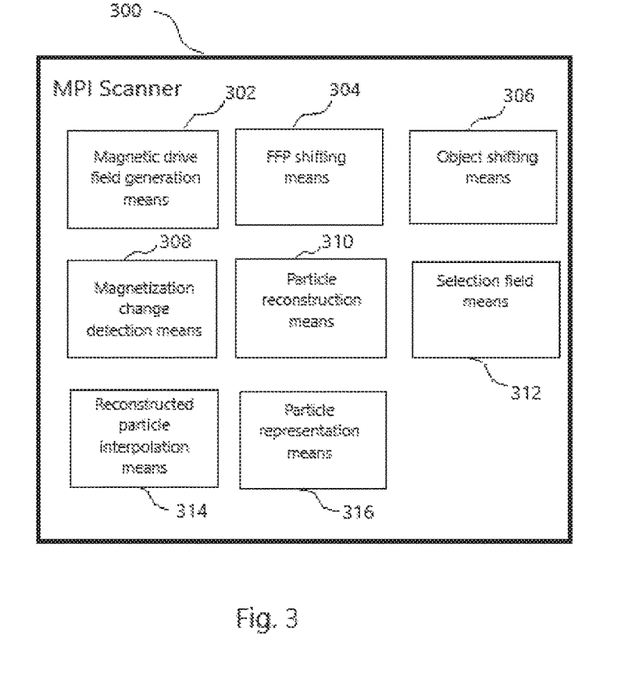
FIG. 3 is a block diagram of an inventive MPI scanner for tomographic imaging of an object.

As shown in FIG. 3, the object is further achieved by an inventive MPI scanner 300 for tomographic imaging of an object having magnetic particles distributed in the interior of the object and having a pre-known magnetic effectiveness. The MPI scanner exhibits means for generating a selection field having a predetermined magnetic-field gradient in at least one field-free point (FFP) in a predetermined scan plane 312, means for generating a time-dependent, periodic magnetic drive field having a predetermined maximum frequency 302, means for repeatedly shifting the at least one FFP along a predetermined closed trajectory having a pre-known repetition time in the scan plane 304, means for moving the object through the scan plane along a predetermined feed direction at a predetermined feed velocity 306, means for detecting the change in the magnetization state of the magnetic particles at the locations, traversed by the at least one FFP, in the interior of the object 308, means for reconstructing the local particle concentrations on the locations, traversed by the at least one FFP, relative to an object coordinate system 310, means for interpolating the reconstructed particle concentrations onto the locations, not traversed by at least one FFP, in the interior of the object 314, means for generating a representation of the particle concentration distribution in the interior of the object 316, and is characterized in that
the means for interpolating 314 are further suitable for interpolating the particle concentrations, reconstructed at path section end points of path sections along the feed direction, onto path section intermediate points taking into account the feed velocity.

The sub-claims specify advantageous designs of the invention.

Goodwill et al. describes that an object lying on a bench can be moved through a scan plane with an FFL. Here Goodwill et al. do not use the advantages of the raw-data acquisition with one FFP, but only the sum signal of the FFL. The decisive improvement by the method proposed here is now the interpolation of suitable points of the measurement trajectory in the axial direction. This principle can be used both for the FFP based and also for the FFL based trajectory.

Both the frequency at which the FFP or the FFL is moved in the scan plane and the feed velocity of the bench here determine the degree of sub-sampling. For if the frequency is low and the feed velocity is high, the FFP or the FFL then moves through the three-dimensional FOV referred to object coordinates and thus only sweeps across a part of all spatial points—or voxels—of the FOV. If for example the FFL rotates about its center at a predetermined frequency, while the bench is shifted, then in object coordinates it describes a helical surface. Evidently the FFL at no point in time passes through voxels outside the helical surface, and if the feed velocity is increased, the number of these voxels and thus the degree of sub-sampling increases.

The electrotechnic effort for producing an MPI measurement using FFL is more complex than that using an FFP.

It is therefore a preferred design of the invention to generate only a single FFP instead of an FFL and to shift it in a two-dimensional scan plane. In this case, the local particle concentration in the vicinity of the current location of the FFP can be inferred directly from the MPI measurement values from the FFP at any point in time.

When the object is moved through the scan plane, the FFP moves on a possibly complicated trajectory in the FOV. The measurement data are for example and preferably detected during the course of the MPI measurement on Cartesian object coordinates that themselves are pre-known functions $x(t)$, $y(t)$, $z(t)$ of the measurement time t.

For example and preferably, $x(t)$ and $y(t)$ describe a trajectory closed in the scan plane having a plurality of crossing points. In this case it can be the two-dimensional Lissajous trajectories mentioned initially.

The feed velocity $v_T$ along the z axis during the MPI measurement is constant preferably at least in a predetermined examination region of the object, i.e., $z(t)=z_0+v_T*t$ holds there with a pre-known constant offset $z_0$.

The entirety of all spatial points $(x(t), y(t), z(t))$ traversed by the FFP describes the three-dimensional FFP trajectory in the FOV. It exhibits no intersection points with itself and possibly does not traverse each voxel of the FOV.

During a repetition time $T_R$ of the two-dimensional, closed trajectory the FFP in the FOV covers a feed path $v_T*T_R$ along the z axis that is to be termed the "expansion" of the two-dimensional to the three-dimensional FFP trajectory.

The following statements hold for the expansion:
1. The expansion increases with the feed velocity at which the object is moved through the scan plane.
2. The expansion increases with the repetition time, i.e. when the maximum frequency of the drive field is reduced with an essentially constant frequency ratio $f_y/f_x$ and constant path length of the trajectory.
3. If the expansion amounts to at most the edge length $\Delta x$ of the voxels of the FOV then no sub-sampling occurs by the feed.
4. If the expansion amounts to $p*\Delta x$ with p greater than one, then a sub-sampling of the FOV occurs caused by the feed, the degree of sub-sampling approximately amounting to $(p-1)/p$.

For the statement 3 it is to be noted that within a layer of the FOV there may well be voxels that are not traversed by the FFP. This sub-sampling inside the scan plane can also occur if there is no feed of the object through the scan plane. The cause lies in the choice of the two-dimensional FFP trajectory or the discretization that possibly samples incompletely. The already mentioned U.S. 2012/153949 A1 deals with improvement possibilities with respect to this issue so that the interested reader is specifically referred thereto. This improvement possibilities are not taken into account below. In the context of the present description, it is solely the sub-sampling by the feed that is to be considered.

It is now the basic idea of the invention that if sub-sampling caused by the feed occurs, not all voxels of the FOV for which no MPI measurement values can be detected can be equally problematic during the subsequent data interpolation. Rather voxels exist on which still robust estimates can be calculated from the reconstructed particle concentrations along the three-dimensional FFP trajectory even in the case of a high degree of sub-sampling. According to the invention, they are situated on path sections along the feed direction in each case between two path section end points for which measured particle concentrations exist.

Figure 2:
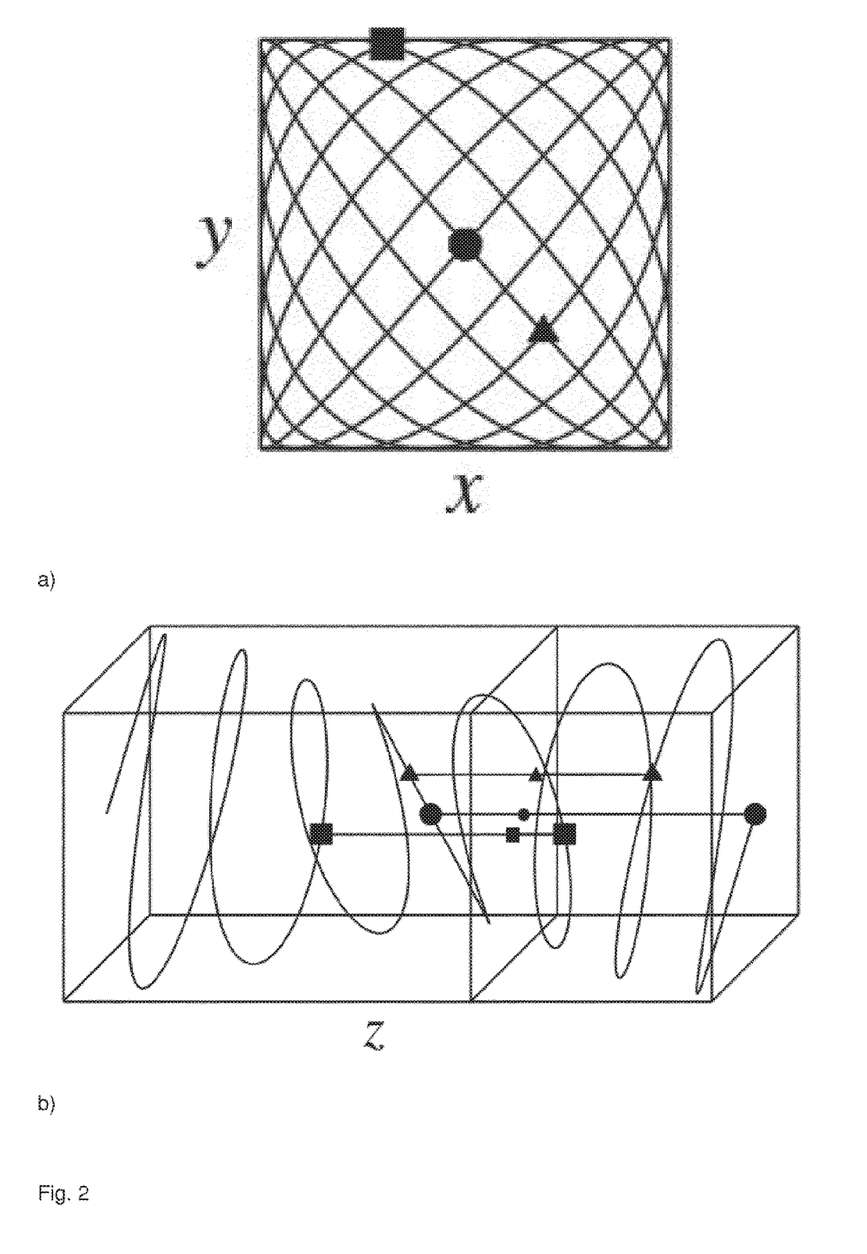

In FIG. 2 a) there is drawn an FFP trajectory closed in the scan plane having crossing points. Three arbitrarily choosing crossing points are marked with a circle, a triangle and a square. The relative shift between FFP and object along the z axis produces the three-dimensional—also: expanded—FFP trajectory in the FOV referred to object coordinates, as drawn in FIG. 2 b). At this point precisely one pass of the FFP trajectory having a return into the starting point in the scan plane is drawn, i.e. the expansion precisely corresponds to the illustrated width of FIG. 2 b).

The expanded FFP trajectory does not intersect itself, but the previously marked crossing points in the scan plane now define path sections in the object coordinate system that extend precisely along the z axis. Particle concentrations in each case reconstructed from the MPI measurement now exist at both end points of these path sections so that the robust interpolation onto the path section intermediate points is possible as long as the length of a path section does not exceed the width of the point spread function $\Delta x$.

According to the invention, path sections where robust interpolation is possible are determined in that the pre-known points in time when the FFP traverses the likewise pre-known crossing points, are converted taking into account the feed velocity into path lengths and it is checked whether they are smaller than $\Delta x$. During the measurement, the feed velocity is preferably constant and known. In this case, the robust interpolatable voxels of the FOV are already established prior to the measurement. But even if the feed velocity should vary during the measurement, the invention can be utilized on the precondition that the feed velocity is recorded continuously together with the measurement data or it is already known as a function of time.

In principle, the expansion of the FFP trajectory can be controlled by means of the frequency ratio or the repetition time of the trajectory, but is preferably controlled by choosing the feed velocity. However, control by means of the repetition time, where the drive field frequencies are varied, entails the shifting of the crossing points and makes the evaluation more difficult on so far for the case that the crossing points are not determined dynamically—during data acquisition—, but are calculated a priori and are stored in tables.

From FIG. 2 b) it is evident that even for the case that the expansion amounts to a multiple of □x, still path sections can exist between the crossing points that are shorter than □x and insofar permit robust interpolation onto the path section intermediate points.

If in particular and as an example the case is considered that the expansion amounts to $2*\Delta x$ this means initially that the FFP, during a single pass of the two-dimensional closed trajectory in the scan plane, i.e. during the repetition time $T_R$, traverses in the three-dimensional FOV an area comprising two layers of voxels having the edge length □x. However, about half of these voxels will not be traversed by the FFP, i.e. the degree of sub-sampling by the feed amounts to approximately 50%.

Nevertheless still about half of all path sections between the crossing points is still shorter than □x and the path section intermediate points of these path sections can be interpolated in a robust manner. These already permits a part interpolation of both layers. If it is further considered that the trajectory is traversed repeatedly and thus leading and trailing MPI measurements are present, it is possible to interpolate further voxels in a robust manner. This is because each closed FFP trajectory can be divided into half trajectories of equal length starting and ending at crossing points and can be joined again, swapped in terms of time. To put it differently: the second half of an FFP trajectory can be joined to the first half of the subsequent FFP trajectory and used for this new trajectory likewise crossing points and connecting paths for interpolation.

To complete the interpolation onto all remaining voxels or spatial points of the FOV not originally traversed by the FFP, the remaining data gaps can be closed using a suitable algorithm according to the prior art, for example from CT image reconstruction, using the results of the path sections that have been interpolated with priority. Here it is particularly preferable that the interpolated path sections are present in a manner distributed along the z axis, i.e., in each z plane areas are available with relatively reliable data, either measured or robustly interpolated, from the inventive method.

In principle, the arguments already mentioned also hold when the expansion amounts to an arbitrary multiple of □x. However, the robustly interpolatable path sections between the crossing points become increasingly scarce with the growing expansion and the reliable areas in each z plane becomes increasingly smaller. At some point in time, the image obtained is dominated by artifacts of the interpolation.

However it is to be pointed out that at x=±Δx/2 the point spread function from FIG. 1 b) does not abruptly fall to zero but exhibits a larger reach. It is also possible to pose oneself the question when carrying out the invention, whether path sections having a length greater than □x are to be used for prioritized interpolation. As is often the case, the necessary degree of sub-sampling has to be weighed against the artifact tolerance in the images generated.

At present it is assumed that the expansion of the FFP trajectory can amount to between □x and 3*Δx without incurring larger disadvantageous for MPI imaging. Under favorable circumstances, an expansion up to 5*Δx could still lead to useful results. However, the degree of sub-sampling here still amounts to approximately 80% and considerable artifacts are then to be expected.

The advantage of the invention is illustrated using the following example of a medical MPI scanner whose FOV can contain the entire body of an adult patient.

A medical MPI scanner for example exhibits a displaceable table for taking up a lying patient, that by means of an electric motor can move the patient lengthwise through a coil arrangement. I.e. in a general form, means for moving the object through the scan plane along a predetermined feed direction 306 are provided.

The coils generate a selection and drive field such that an FFP can be generated in a scan plane at right angles to the table feed direction and can be displaced. I.e. in a general form, means for generating a selection field having a predetermined magnetic-field gradient in at least one field-free point (FFP) in a predetermined scan plane 312 and means for generating a time-dependent periodic magnetic drive field having a predetermined maximum frequency 302 and means for repeatedly displacing the at least one FFP along a predetermined closed trajectory at a pre-known repetition time in the scan plane 304 are provided.

The scan plane contains an FOV having a diameter of 0.5 m. For setting up a magnetic-field gradient having the absolute value G=1 T/m in the FFP, inside the FOV a magnetic-field amplitude of approximately 0.25 T has to be generated.

The FFP for example runs on a Lissajous trajectory in the scan plane at a frequency ratio according to Equation (2).

The MPI scanner further contains means for detecting the change in the magnetization state of the magnetic particles at the locations in the interior of the object 308, that the at least one FFP traverses. These means for detecting can for example be designed as detection coils or as magnetic-field sensors.

The MPI scanner further also features means for reconstructing the local particle concentration at the locations traversed by the at least FFP relative to an object coordinate system 310. These means for reconstructing can for example be provided by a computer unit that is hardware-programmable or set up program-technically or a combination therefrom.

The MPI scanner furthermore also exhibits means for interpolating the reconstructed particle concentrations onto the locations, not traversed by at least one FFP, in the interior of the object 314. The means for interpolating are further suitable for interpolating the particle concentrations, reconstructed at path section end points of path sections along the feed direction, onto path section intermediate points taking into account the feed velocity.

These means for interpolating can for example also be provided by a computer unit that is hardware-programmed or set up program-technically or a combination therefrom, it having to be noted here that the computer unit that is hardware-programmed or set up program-technically at the same time can also support other steps of the method.

Over and above this, the MPI scanner also exhibits means for generating a representation of the particle concentration distribution in the interior of the object 316. As an example, by means of a display unit such as e.g. a screen or a projector the particle concentration distribution in the interior of the object can be visualized suitably, e.g. color coded.

When the magnetic particles administered to the patient prior to the MPI measurement have a magnetic effectiveness of $X_S=3*10^{-3}$ T, the width of the point spread function in the FFP is Δx=3 mm, and for a sufficiently dense sampling of the scan plane, approximately $$N_d = 0.5 \text{ m}/3 \text{ mm} = 167 \quad (3)$$

crossing points of the Lissajous trajectory along each diameter are required.

As an example, the maximum drive field frequency, here fx, is set to be 100 Hz so as to reliably avoid peripheral nerve stimulation. By definition, the repetition time of the trajectory then amounts to $$T_R = N_d/f_y = (N_d+1)/f_x = 168/100 \text{ Hz} = 1.68 \text{ s}. \quad (4)$$

This estimate is orders of magnitude above the repetition times of FFP trajectories in the MPI scanners realized up to this date.

In principle, for an MPI scanner having a scan plane through which a human person is to be moved, it is to be provided that the at least one field-free point is displaced along a closed trajectory having a repetition time above 500 milliseconds, preferably above one second.

Without a sub-sampling caused by the feed, a full body scan the patient having a body length of e.g. 1.80 m would have to be carried out at a feed velocity of $$v_T = 3 \text{ mm}/1.68 \text{ s} = 1.79 \text{ mm/s} \quad (5)$$

and would require a total of 1008 s=16.8 min. Using the invention, this time can now be effectively divided by two or even three without excessive artifacts being produced in the MPI images as a result.

In a preferred design, the maximum frequency of the drive field is predetermined, and the degree of sub-sampling is solely established by the choice of the feed velocity by the user. According to the invention, it is to be set as $$v_T = p * X_S / (G * T_R) \quad (6)$$

p being a number greater than one and smaller than five. p is preferably greater than one and at most three.

It is to be emphasized here, that it is a preferred design of the invention to establish the maximum drive field frequency, i.e. the highest-frequency part of the periodic drive field, at a frequency of below 1000 Hz, preferably below 200 Hz, particularly preferably about 100 Hz in the case of a human full body scanner.

This definition is motivated physiologically for living human persons and gives rise to sub-sampling the FOV and to applying the invention; however, it is not compulsory. There can also be an occasion for sub-sampling for other reasons, if for example a—quite possibly inanimate—object is to be exposed only to a moderate magnetic induction or it is possibly desired to move it through the scan plane at a very high velocity, e.g. on a conveyor belt.

For the sake of completeness it shall be noted that moving the object through the scan plane can evidently also be realized in an alternative manner in that a moveable coil arrangement that generates all necessary magnetic fields in thus sets up a scan plane, is guided past the object at rest in such a manner that the scan plane is moved through the object. In the meaning of the invention, both variations are to be regarded as equivalent.

Aspects of the invention can be readily also embodied in software and/or in computer devices set up program-technically.

The invention claimed is:

1. A method for tomographic imaging an object having magnetic particles distributed in the interior of the object and having a pre-known magnetic effectiveness, comprising the following steps
   generating a selection field having a predetermined magnetic-field gradient in at least one field-free point (FFP) in a predetermined scan plane,
   generating a time-dependent, periodic magnetic drive field having a predetermined maximum frequency,
   repeatedly shifting the at least one FFP along a predetermined closed trajectory having a pre-known repetition time in the scan plane, moving the object through the scan plane along a predetermined feed direction at a predetermined feed velocity,
   detecting the change in the magnetization state of the magnetic particles at the locations, traversed by the at least one FFP, in the interior of the object,
   reconstructing the local particle concentrations at the locations, traversed by the at least one FFP, relative to an object coordinate system,
   interpolating the reconstructed particle concentrations onto the locations, not traversed by at least one FFP, in the interior of the object,
   generating a representation of the particle concentration distribution in the interior of the object,
   wherein
   interpolating the particle concentrations, reconstructed at path section end points of path sections along the feed direction, onto path section intermediate points taking into account the feed velocity.

2. The method according to claim 1, wherein the maximum frequency of the periodic magnetic drive field is predetermined to be smaller than 1000 Hz, preferably smaller than 200 Hz, particularly preferably smaller than 100 Hz.

3. The method according to one of the preceding claims, wherein precisely one FFP is generated and shifted repeatedly along a closed trajectory in the scan plane, the trajectory exhibiting crossing points in the scan plane.

4. The method according to claim 3, wherein the crossing points, that are spaced apart in the object coordinate system along the feed direction, of the trajectory, closed in the scan plane, are used as path section end points.

5. The method according to claim 3, wherein the repetition time of the trajectory is designed to be greater than 500 milliseconds, preferably greater than 1 second.

6. The method according to claim 1, the repetition time $T_R$ of the closed trajectory in the scan plane and the predetermined magnetic-field gradient G in the at least one FFP and the magnetic effectiveness $X_S$ of the magnetic particles are used for predetermining the maximum feed velocity.

7. The method according to claim 6, wherein the maximum feed velocity $v_T$ is predetermined to be $v_T = p * X_S / (G * T_R)$, p being a number greater than one and smaller than five, preferably at most three.

8. The method according to claim 1, wherein the feed velocity is kept constant during the detection of the change of the magnetization state of the magnetic particles in at least one predetermined investigation region of the object.

9. An MPI scanner for tomographic imaging of an object having magnetic particles distributed in the interior of the object and having a pre-known magnetic effectiveness, comprising
   means for generating a selection field having a predetermined magnetic-field gradient in at least one field-free point (FFP) in a predetermined scan plane,
   means for generating a time-dependent, periodic magnetic drive field having a predetermined maximum frequency,
   means for repeatedly shifting the at least one FFP along a predetermined closed trajectory having a pre-known repetition time in the scan plane,
   means for moving the object through the scan plane along a predetermined feed direction at a predetermined feed velocity,
   means for detecting the change in the magnetization state of the magnetic particles at the locations, traversed by the at least one FFP, in the interior of the object,
   means for reconstructing the local particle concentrations at the locations, traversed by the at least one FFP, relative to an object coordinate system,
   means for interpolating the reconstructed particle concentrations onto the locations, not traversed by at least one FFP, in the interior of the object,
   means for generating a representation of the particle concentration distribution in the interior of the object,
   wherein
   the means for interpolating are further suitable for interpolating the particle concentrations, reconstructed at path section end points of path sections along the feed direction, onto path section intermediate points taking into account the feed velocity.

10. The MPI scanner according to claim 9, wherein the maximum frequency of the periodic magnetic drive field is predetermined to be smaller than 1000 Hz, preferably smaller than 200 Hz, particularly preferably smaller than 100 Hz.

11. The MPI scanner according to claim 9, wherein precisely one FFP is generated and shifted repeatedly along a closed trajectory in the scan plane, the trajectory exhibiting crossing points in the scan plane.

12. The MPI scanner according to claim 11, wherein the crossing points, that are spaced apart in the object coordinate system along the feed direction, of the trajectory, closed in the scan plane, are used as path section end points.

13. The MPI scanner according to claim 11, wherein the repetition time of the trajectory is designed to be greater than 500 milliseconds, preferably greater than 1 second.

14. The MPI scanner according to claim 9, wherein the repetition time $T_R$ of the closed trajectory in the scan plane and the predetermined magnetic-field gradient G in the at least one FFP and the magnetic effectiveness $X_S$ of the magnetic particles are used for predetermining the maximum feed velocity.

15. The MPI scanner according to claim 9, wherein the feed velocity is kept constant during the detection of the change of the magnetization state of the magnetic particles in at least one predetermined investigation region of the object.

* * * * *